(12) United States Patent
Hill

(10) Patent No.: US 7,205,012 B1
(45) Date of Patent: Apr. 17, 2007

(54) SCAR REDUCING AND MASSAGE EMOLLIENT

(76) Inventor: Wendy L. Hill, 4758 Appleton St., San Diego, CA (US) 92117

( * ) Notice: Subject to any disclaimer, the term of this patent is extended or adjusted under 35 U.S.C. 154(b) by 126 days.

(21) Appl. No.: 11/065,661

(22) Filed: Feb. 25, 2005

(51) Int. Cl.
*A01N 65/00* (2006.01)

(52) U.S. Cl. ...................... 424/764; 424/765; 424/745; 424/744

(58) Field of Classification Search ................ 424/764, 424/765, 745, 744
See application file for complete search history.

(56) References Cited

U.S. PATENT DOCUMENTS

| | | | |
|---|---|---|---|
| 5,266,318 A | * | 11/1993 | Taylor-McCord |
| 5,578,312 A | | 11/1996 | Parrinello |
| D411,747 S | | 6/1999 | Kokenge et al. |
| 6,099,849 A | | 8/2000 | Mansouri |
| 6,447,788 B1 | | 9/2002 | Strathausen |
| 6,475,476 B1 | | 11/2002 | Fluker |
| 6,524,626 B2 | | 2/2003 | Chen |
| 2002/0086039 A1 | | 7/2002 | Lee et al. |

OTHER PUBLICATIONS http://www.botanical.com/botanical/mgmh/m/marigo16.html. "Marigold", downloaded Aug. 17, 2006.*
http://www.botanical.com/botanical/mgmh/c/chammo49.html. "Chamomiles", downloaded Aug. 17, 2006.*
http://en.wikipedia.org/wiki/Chamomile. "Chamomile", downloaded Aug. 17, 2006.*
http://en.wikipedia.org/wiki/Comfrey. "Comfrey", downloaded Aug. 17, 2006.*
http://www.botanical.com/botanical/mgmh/c/comfre92.html. "Comfrey", downloaded Aug. 17, 2006.*
http://en.wikipedia.org/wiki/Rose. "Rose", downloaded Aug. 17, 2006.*
http://www.botanical.com/botanical/mgmh/r/rosema17.html. "Rosemary", downloaded Aug. 17, 2006.*
http://www.ibiblio.org/pfaf/cgi-bin/arr_html?Rosmarinus+officinalis&CAN=COMIND. "Rosmarinus officinalis", downloaded Aug. 17, 2006.*
http://www.mountainroseherbs.com/learn/geranium.php. "Rose Geranium Essential Oil", downloaded Aug. 17, 2006.*

* cited by examiner

*Primary Examiner*—Michele Flood

(57) ABSTRACT

A scar reducing and massage emollient includes the mixing together of calendula flowers, chamomile flowers, comfrey leaf, rose petals, rosemary and rose geranium to form a herb mixture. Positioning the herb mixture in a cooking vessel and covering the herb mixture with almond oil and olive oil and heating the cooking vessel at a temperature below the boiling point of the olive and almond oils to define a heated mixture. Straining the heated mixture through cheesecloth to define a strained oil. Melting beeswax and mixing it with shea butter, lavender oil, Ylang Ylang oil, *Aloe vera* gel, jojoba oil, wheat germ oil, evening primrose oil and the strained oil to define an emollient. Positioning the emollient in at least one container.

2 Claims, 1 Drawing Sheet

INGREDIENTS

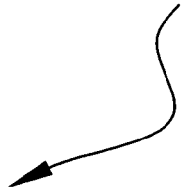

- 4 cups fresh herbs/flowers or 1-1/2 cups dried herbs/flowers
- 7-1/2 cups almond and olive oils
- 10 ounces beeswax
- 4-6 ounces african shea butter
- 1 ounce essential oils, 1/2oz lavender and 1/2oz Ylang Ylang
- 1/2 cup aloe vera gel
- 1 tablespoon jojoba oil
- 1 tablespoon wheat germ oil
- 1 tablespoon borage oil
- 1 tablespoon evening primrose oil
- Combination of herbs/flowers listed above would be formulated from:
- 1 cup calendula flowers
- 1 cup chamonile flowers
- 1 medium size comfrey leaf
- 1/2 cup rose petals
- 1/2 cup lavender flowers
- 1/4 cup rosemary
- 1/4 cup rose geranium

FIG.1

SCAR REDUCING AND MASSAGE EMOLLIENT

BACKGROUND OF THE INVENTION

1. Field of the Invention

The present invention relates to scar reducing mixtures and more particularly pertains to a new scar reducing mixture for reducing scar tissue and for serving as a general all-purpose massage emollient.

2. Description of the Prior Art

The use of scar reducing mixtures is known in the prior art. However, these have not included a plurality of essential oil extracts and herbs which are well known to have certain healing and muscle relaxing properties. For this reason, such a mixture is required which is particularly well adapted at reducing scar tissue and which may be used for general massage purposes.

SUMMARY OF THE INVENTION

The present invention meets the needs presented above by generally comprising the mixing together of calendula flowers, chamomile flowers, comfrey leaf, rose petals, rosemary and rose geranium to form a herb mixture. Positioning the herb mixture in a cooking vessel and covering the herb mixture with almond oil and olive oil and heating the cooking vessel at a temperature below the boiling point of the olive and almond oils to define a heated mixture. Straining the heated mixture through cheesecloth to define a strained oil. Melting beeswax and mixing it with shea butter, lavender oil, Ylang Ylang oil, Aloe vera gel, jojoba oil, wheat germ oil, evening primrose oil and the strained oil to define an emollient. Positioning the emollient in at least one container.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawing wherein:

FIG. 1 is a schematic view of the ingredients of a scar reducing and massage emollient according to the present invention.

DESCRIPTION OF THE PREFERRED EMBODIMENT

With reference now to FIG. 1, a new scar reducing mixture embodying the principles and concepts of the present invention and generally designated by the reference numeral 10 will be described.

As generally shown in FIG. 1, the scar reducing and massage emollient 10 generally comprises mixing together 1 cup calendula flowers (*Calendula officinalis*), 1 cup chamomile (*Chamaemelum nobile*) flowers, 1 medium size comfrey (*Symphytum officinale*) leaf, ½ cup rose (*Rosa*) petals, ¼ cup rosemary (*Rosmarinus officinalis*) and ¼ cup rose geranium (*Pelargonium roseum*) to form a herb mixture.

The herb mixture is positioned in a cooking vessel and is covered with 3¾ cups of almond oil and 3¾ cups of olive oil. The oils and herb mixture are then heated for 3 hours at a temperature below the boiling point of the olive and almond oils to define a heated mixture. This heated mixture is then strained through cheesecloth and the strained oil retrained.

Beeswax, 10 ounces thereof, is melted. The melted beeswax is mixed together with 5 ounces of shea (*Butyrospermum parkii*) butter, ½ ounce of lavender oil, ½ ounce of Ylang Ylang (*Cananga odorata*) oil, ½ cup *Aloe vera* gel, 1 tablespoon jojoba oil (*Simmondsia chinesis*), 1 tablespoon wheat germ oil, 1 tablespoon evening primrose (*Primula*) oil and the strained oil to define the emollient. The emollient is then placed in at least one container which is preferably airtight and resealable.

In use, the emollient is rubbed on the skin for a variety of health effects. In particular, the emollient may be rubbed on scar tissue and rubbed therein. The friction caused by movement against the scar tissue, as well as the ingredients of the emollient, aids in the healing of the scar tissue. Additionally, the emollient may be used for general massage use and for the softening of the skin.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A method of making a scar reduction emollient, said method comprising the steps of:

mixing together calendula flowers, chamomile flowers, comfrey leaf, rose petals, rosemary and rose geranium to form a herb mixture;

positioning the herb mixture in a cooking vessel and covering the herb mixture with almond oil and olive oil and heating the cooking vessel at a temperature below the boiling point of the olive and almond oils to define a heated mixture;

straining the heated mixture through cheesecloth to define a strained oil;

melting beeswax and mixing together said beeswax with shea butter, lavender oil, Ylang Ylang oil, *Aloe vera* gel, jojoba oil, wheat germ oil, evening primrose oil and said strained oil to define said emollient; and positioning said emollient in at least one container.

2. A method of making a scar reduction emollient, said method comprising the steps of:

mixing together 1 cup calendula flowers, 1 cup chamomile flowers, 1 medium size comfrey leaf, ½ cup rose petals, ¼ cup rosemary and ¼ cup rose geranium to form a herb mixture;

positioning the herb mixture in a cooking vessel and covering the herb mixture with 3¾ cups of almond oil and 3¾ cups of olive oil and heating the cooking vessel for about 3 hours at a temperature below the boiling point of the olive and almond oils to define a heated mixture;

straining the heated mixture through cheesecloth to define a strained oil;

melting 10 ounces of beeswax and mixing together said beeswax, 5 ounces of shea butter, ½ ounce of lavender oil, ½ ounce of Ylang Ylang oil, ½ cup *Aloe vera* gel, 1 tablespoon jojoba oil, 1 tablespoon wheat germ oil, 1 tablespoon evening primrose oil and said strained oil to define said emollient; and positioning said emollient in at least one container.

\* \* \* \* \*